United States Patent
Maggiano et al.

(10) Patent No.: US 9,232,892 B2
(45) Date of Patent: Jan. 12, 2016

(54) APPLANATION TONOMETER AND METHOD FOR MEASURING THE INTRAOCULAR PRESSURE OF THE EYE

(75) Inventors: John M. Maggiano, Santa Ana, CA (US); Steven E. Maurath, Santa Ana, CA (US); Michael Moewe, San Francisco, CA (US)

(73) Assignee: LightTouch, LLC, Carson City, NV (US)

( * ) Notice: Subject to any disclaimer, the term of this patent is extended or adjusted under 35 U.S.C. 154(b) by 1091 days.

(21) Appl. No.: 13/284,022

(22) Filed: Oct. 28, 2011

(65) Prior Publication Data

US 2012/0108941 A1    May 3, 2012

Related U.S. Application Data

(60) Provisional application No. 61/456,168, filed on Nov. 3, 2010.

(51) Int. Cl.
| | |
|---|---|
| *A61B 3/16* | (2006.01) |
| *A61B 3/10* | (2006.01) |
| *A61B 3/14* | (2006.01) |

(52) U.S. Cl.
CPC ... *A61B 3/16* (2013.01); *A61B 3/10* (2013.01); *A61B 3/14* (2013.01)

(58) Field of Classification Search
CPC .................................... A61B 3/16; A61B 3/10
USPC .......... 600/398–406, 476, 478; 351/200, 205, 351/211–213, 220, 221; 359/227, 229, 232
See application file for complete search history.

(56) References Cited

U.S. PATENT DOCUMENTS

| | | | |
|---|---|---|---|
| 3,287,957 A | 11/1966 | Martens | |
| 5,070,875 A | 12/1991 | Falck et al. | |
| 5,203,331 A | 4/1993 | Draeger | |
| 6,413,214 B1 | 7/2002 | Yang | |
| 6,776,756 B2 | 8/2004 | Feldon et al. | |
| 6,981,946 B2 | 1/2006 | Davidson | |

(Continued)

OTHER PUBLICATIONS

Zhang, et al. "Development of an optical probe to measure the flattened area of ocular cornea." Chinese Optics Letters 8.1 (2010): 103-106. Retrieved from <http://www.opticsinfobase.org/col/abstract.cfm?uri=col-8-1-103> on Jan. 20, 2015.*

(Continued)

*Primary Examiner* — Devin Henson
*Assistant Examiner* — David J McCrosky
(74) *Attorney, Agent, or Firm* — Morland C. Fische

(57) ABSTRACT

An applanation tonometer for measuring intraocular pressure (IOP) so that the health of a human or animal eye can be determined. The applanation tonometer includes a prism having a contact tip at one end to be moved into contact with and lightly touched against the cornea or the eye. Incident laser light is transmitted inwardly through the prism to the contact tip at which some of the light is decoupled and lost though the contact tip depending upon the area of contact between the contact tip and the cornea. The remaining light is reflected by the contact tip outwardly through the prism. A photo defector which is responsive to the light reflected by the contact tip of the prism and a force detector which is responsive to the pressure at the area of contact between the contact tip and the cornea generate paired force and area data pairs that are processed to measure IOP.

13 Claims, 5 Drawing Sheets

(56) References Cited

U.S. PATENT DOCUMENTS

| | | |
|---|---|---|
| 7,473,231 B2 | 1/2009 | Falck, Jr. et al. |
| 7,659,971 B2 * | 2/2010 | Warden ................ A61B 3/1015 356/124 |
| 7,909,765 B2 | 3/2011 | Luce |
| 2004/0236204 A1 | 11/2004 | Feldon et al. |
| 2007/0173713 A1 | 7/2007 | Falck, Jr. et al. |

OTHER PUBLICATIONS

Ma, Jianguo. "Cone prism: principles of optical design and linear measurement of the applanation diameter or area of the cornea." Applied optics 38.10 (1999): 2086-2091. Retrieved from <http://www.opticsinfobase.org/ao/abstract.cfm?uri=ao-38-10-2086> on Jan. 20, 2015.*

* cited by examiner

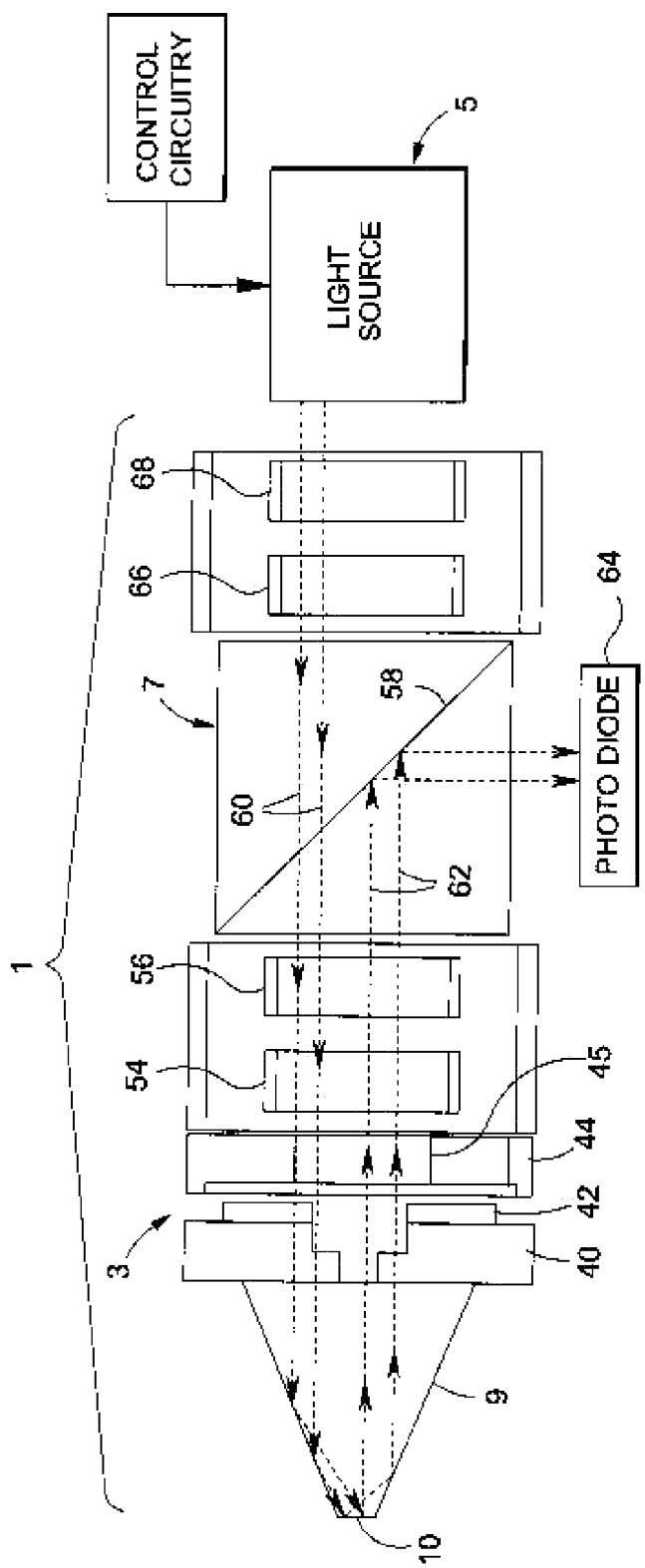
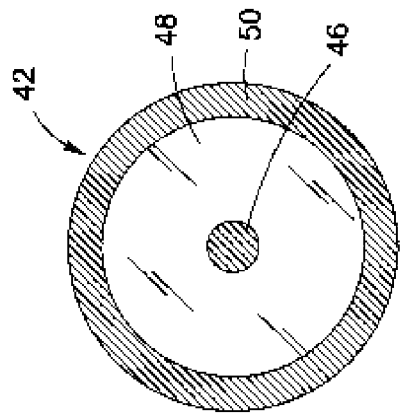
FIG. 3
FIG. 4

APPLANATION TONOMETER AND METHOD FOR MEASURING THE INTRAOCULAR PRESSURE OF THE EYE

CROSS-REFERENCE TO RELATED APPLICATIONS

This application is related to Provisional Patent Application No. 61/456,168 filed Nov. 3, 2010.

BACKGROUND OF THE INVENTION

1. Field of the Invention

This invention relates to an applanation tonometer for providing a measurement of the intraocular fluid pressure (IOP) inside the eye of a human or animal patient. The applanation tonometer herein disclosed has means responsive to both the contact force of the tonometer against the cornea and the touch contact area of the tonometer with the cornea so that paired force and area data is collected, whereby IOP can be accurately measured with minimal dwell time on the cornea and discomfort to the patient.

2. Background Art

A tonometer is a non-invasive instrument which has heretofore been used to measure pressure or tension in human or veterinary tissues. In the human body, intraocular fluid pressure in the eye (IOP) is measured to provide basic information for the diagnosis and treatment of glaucoma and related eye disease.

Ease of application, accuracy and sterility of a tonometer are paramount in medical applications. One instrument which is known to provide highly accurate IOP measurements is the Goldmann applanation tonometer (GAT). A quasi-scientific basis to acquire accurate IOP measurements is referred to as the Imbert-Fick principle. According to this principle, IOP is determined by a calculation of the contact force applied by a tip or the GAT against the cornea divided by area of contact. That is, determining IOP with the GAT relies upon the contact tip covering an applanation area to a fixed diameter of 3.06 mm. The applied force necessary to reach the requisite applanation area is adjusted manually by the healthcare physician or technician. Because the dwell time of the contact tip on the cornea is typically measured in seconds, at topical anesthesia is necessary for the eye. Force and area measurements made by the GAT after multiple touch contacts with corneas of eyes with a range of IOPs form the basis of a nomogramn-derived inference of IOP with respect to a compilation of direct cannula measurements of a population of animal and human eyes.

On occasion, the moving parts of the GAT may jam which can interfere with the effectiveness of the IOP testing. Moreover, the relatively long dwell time required for the contact tip to press correctly against the cornea and the need to apply a topical anesthesia as a result thereof may increase patient discomfort and tissue safety concerns. In this same regard, it would be preferable to limit data acquisition to a single light touch in most cases while providing an instantaneous confirmation to the healthcare professional of either a successful or an unsuccessful pressure test of a patient's eye.

SUMMARY OF THE INVENTION

In general terms, an applanation tonometer with no moving parts is disclosed according to the preferred embodiment to provide an accurate measurement of the intraocular fluid pressure (IOP) inside a human or animal eye in order to make information available for the diagnosis and treatment of glaucoma and other ocular health issues. The applanation tonometer includes a prism assembly at a proximal end thereof, a laser module at a distal end, and an intermediate beam splitter module between the prism assembly and the laser module.

The prism assembly of the applanation tonometer includes a conical prism tat tapers to a (e.g., circular) contact tip. The contact tip has an ideal diameter of between 1 to 8 mm. Lying opposite the contact tip of the prism is a piezo element that is responsive to the force generated as the contact tip is pressed against the cornea while approaching, during and following cornea saturation and full applanation. A light ring having a light absorbing center, a light-absorbing outside area, and a light-transmitting area between the light-absorbing center and outside area is located behind the contact tip of the prism to allow incoming and outgoing light beams to be transmitted inwardly through and outwardly from the prism.

The laser module of the applanation tonometer includes a source of light (e.g., a laser or an LED) that supplies incoming light beams to the prism of the prism assembly by way of a collimator, the beam splitter module and the light ring of the prism assembly. The beam splitter module includes a photo diode and an internal reflective surface that is aligned to reflect to the photo diode outgoing light beams that are reflected internally through the prism before, during and after full applanation. The intensity of the light detected by the photo diode is dependent upon the area of the cornea that is covered by the contact tip as the prism is pressed against the eye.

As the applanation tonometer is moved towards the eye and the contact tip of the prism is pressed against the cornea to achieve applanation, some of the light is decoupled from the incoming light beams that are transmitted inwardly through the prism. The incoming light which is decoupled is transmitted through the contact tip of the prism and lost into the eye. The decoupling is a result of manufacturing the conical prism so that the incoming light beams which are transmitted front the light source or the laser module through the prism are reflected internally to the contact tip of the prism so as to make an angle of between 20 to 27 degrees with a tapered wall of the prism. The remaining light which is not decoupled is reflected internally by and outwardly from the prism through the light ring of the prism assembly and off the reflective surface of the beam splitter assembly to be detected by the photo diode. The output of the piezo element and the photo diode provide force and area data pairs which can be displayed, stored and processed either at the site of the test or remotely to provide a measurement of IOP.

BRIEF DESCRIPTION OF THE DRAWINGS

FIG. 3 shows the applanation tonometer illustrating the paths therethrough of incoming and internally-reflected outgoing light beams;

FIG. 4 shows a light ring through which the incoming and reflected light beams of FIG. 3 are transmitted;

DESCRIPTION OF THE PREFERRED EMBODIMENT

Figure 1:
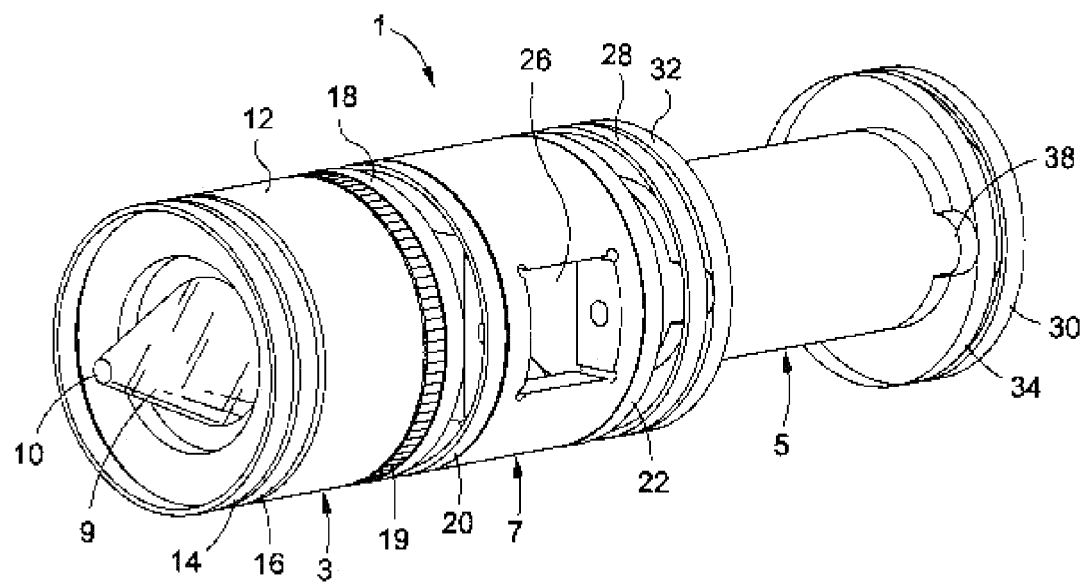
FIG. 1 is a perspective view of an applanation tonometer for measuring intraocular pressure according to a preferred embodiment of the present invention.
Figure 2:
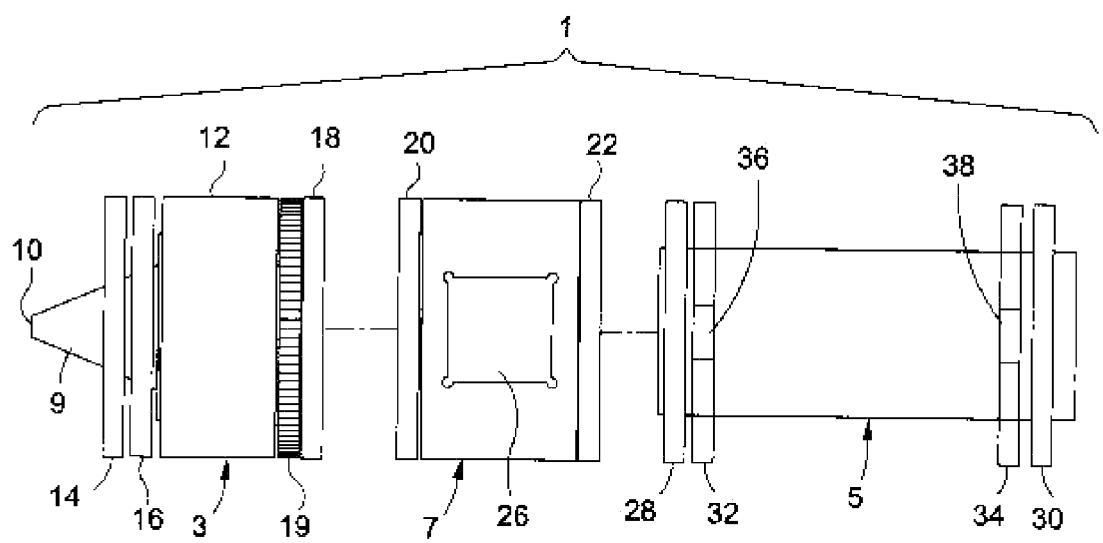
FIG. 2 is an exploded view of the applanation tonometer of FIG. 1.

Referring initially to FIGS. 1 and 2 of the drawings, there is shown a preferred embodiment for an applanation with no moving parts that is adapted to provide healthcare professionals with a measurement of the intraocular fluid pressure inside the eye of a patient to aid in the diagnosis of glaucoma and other ocular health issues such as scleral rigidity. The applanation tonometer 1 includes a prism assembly 3 at a proximal end thereof, a laser module 5 at a distal end, and an intermediate beam splitter module 7 lying therebetween. The prism assembly 3, beam splitter module 7 and laser module 5 are axially aligned with one another.

The prism assembly 3 of the applanation tonometer 1 includes a conical prism 9 (best shown in FIGS. 4 and 5) that is manufactured from glass, acrylic or other suitable light-transmitting material. The proximal end of the prism 9 is ground flat to create a circular contact tip 10 to be moved into contact with the cornea of the eye of a patient for a purpose that will be explained in greater detail hereinafter. The circular contact tip 10 of prism 9 has an ideal diameter of 1-8 mm depending upon the pressure testing application for which the tonometer is employed. The prism assembly 3 includes an outer shell 12 that surrounds and supports the prism 9. A pair of retainer rings 14 and 16 are located in front of the outer shell 12 to hold the prism 9 in axial alignment with the beam splitter module 7. A retainer ring 18 is located behind the outer shell 12 to surround and provide additional support for the prism 9. The prism assembly 3 also includes a piezo ring 19 which surrounds a force-responsive (e.g., piezo) element (designated 44 in FIG. 3).

The beam splitter module 7 of the applanation tonometer 1, which lies between the prism assembly 3 and the laser module 5, has a retainer ring 20 and 22 located at each of the opposite ends thereof to surround and support the beam splitter module 7. An opening or cavity 26 extends radially into the beam splitter module 7 in which to receive a photo detector (such as the photo diode designated 64 in FIG. 3), so that the prism assembly 3 and the photo detector will be held in optical alignment with one another.

Retainer rings 28 and 30 surround and support opposite ends of laser module 5. The laser module 5 also has an alignment ring 32 and 34 at each end thereof lying inside and adjacent one of the retainer rings 28 and 30 to provide self-centering of the laser module with respect to the beam splitter module 7 and the prism assembly 3. Wire ports 36 and 38 are formed in the alignment rings 32 and 34 through which electrical wires (not shown) are connected to the piezo element and the photo diode carried by the intermediate beam splitter module 7. The laser module 5 ideally provides parallel laser light beams to the prism 9 of the prism assembly 3 to be internally reflected by the prism 9 first to the beam splitter module 7 and then to the photo diode of the beam splitter module 7.

FIG. 3 of the drawings shows additional details of the prism assembly 3, laser module 5 and intermediate beam splitter module 7 of the applanation tonometer 1 previously described while referring to FIGS. 1 and 2. The conical prism 9 of the prism assembly 3 is shown extending outwardly from the proximal end of the applanation tonometer so that the contact tip 10 can be briefly pressed against and apply pressure to the patient's cornea to achieve applanation. A flange 40 surrounds the rear of the prism 9 so as to hold a light ring 42 (i.e., a light baffle) in coaxial alignment with the prism 9 so that the prism 9 and light ring 42 will press against the piezo element 44 as the contact tip 10 of the prism 9 is pressed against the cornea. By way of example, the piezo element 44 is manufactured from a metal-doped ceramic disc or the like that is mounted on an electrical substrate or shim and, as will be known to those skilled in the art, is adapted to generate an electrical output voltage signal that is indicative of a change in force as the contact tip 10 of prism 9 is pressed against the patient's cornea during testing. The piezo element 44 has a light-transmitting hole 45 through its center to enable light generated by the laser module 5 to reach the prism assembly 3. Because the piezo element 44 is conventional, the details thereof will not be described.

Referring briefly to FIG. 4 of the drawings, details are provided of the light ring or light baffle 42 that is held by the flange 40 of FIG. 3 adjacent the piezo element 44 and in coaxial alignment with the prism 9 of prism assembly 3. The light ring 42 is preferably a disk (i.e., an optically-pure substrate) manufactured from a lightweight optically-transparent material. Located at the center of the light ring 42 is an optically-opaque (i.e., light-absorbing) dot 46 or the like. The dot 46 is sized and shaped to match the diameter of the circular contact area 10 of the prism 9. Thus, the diameter of dot 46 is ideally between 1 to 8 mm. An optically-transparent ring-shaped area 48 of the light ring 42 surrounds the optically-opaque dot 46. The size of the optically-transparent ring-shaped area 48 will depend upon the size and internal angles of the prism 9. A light absorbing ring-shaped area 50 surrounds the optically-transparent ring-shaped area 48 of light ring 42. The light-absorbing area 50 can be, for example, a coating or a suitable opaque material applied circumferentially around the outside of the substrate of light ring 42. It may thusly be appreciated, and as is illustrated in FIG. 3, both incoming light transmitted from the laser module 5 to the prism 9 and outgoing light internally reflected by the prism 9 to the beam splitter module 7 will pass through the optically-transparent ring-shaped area 48 of light ring 42.

Returning to FIG. 3, the applanation tonometer 1 also includes a pair of conventional light beam expanders and/or collimators 54 and 56 that are located between the prism assembly 3 and the beam splitter module 7 so as to lie in the paths of the incoming light transmitted from the laser module 5 and the outgoing light reflected from the prism 9. As will be known to those skilled in the art, the light beam expanders and collimators 54 and 56 are adapted to focus and absorb stray light and thereby reduce spurious light transmissions in cases where the incoming light from the source is not transmitted as parallel beams. Thus, a combination of expanders and collimators may be used for different applications.

The beam splitter module 7 of the applanation tonometer 1 includes a conventional beam splitter having an internal reflecting surface 58. As will be known to those skilled in the art, incoming parallel light beams 60 being transmitted from the laser module 5 pass through the beam splitter to the prism 9 of the prism assembly 3. The outgoing parallel light beams 62 which are reflected internally by prism 9 are transmitted to and reflected by the reflecting surface 58 of the beam splitter module 7 to the photo diode 64 that is retained within the opening (designated 26 in FIGS. 1 and 2) of module 7. For purpose of convenience in illustration, the incoming and outgoing light beams 60 and 62 are shown traveling in separate paths. However, as will be explained when referring to FIGS. 5 and 6, the incoming and outgoing light beams travel along identical paths between the beam splitter module 7 and the prism assembly 3.

Located between the beam splitter module 7 and the laser module 5 are another pair of conventional light beam expanders and/or collimators 66 and 68. The expanders/collimator 66 and 68 may be identical to those designated 54 and 56 between the prism assembly 3 and beam splitter module 7. The light beam expanders and collimators 66 and 68 also control the incoming light and further ensure that parallel light beams 60 will pass through the beam splitter module 7 to the prism assembly 3. In this regard, it may be appreciated that the pairs of light beam expanders/collimators 54, 56 and 66, 68 located at opposite ends of the beam splitter module 7 cooperate to form a well-known light management assembly.

The laser module 5 is preferably a Class II laser (e.g., a laser diode). However, any other suitable light source (e.g., an LED) may be substituted for the aforementioned laser diode. In the preferred embodiment, incoming parallel-aligned laser light beams generated by the laser module 5 are supplied through the light ring 42 to the prism 9 by way of the beam splitter module 7 and the light beam expander/collimator assemblies at opposite ends of the beam splitter module. In this same regard, it is to be understood that converging or diverging light (as opposed to parallel light beams) may also be supplied to the prism 9.

Figure 5:
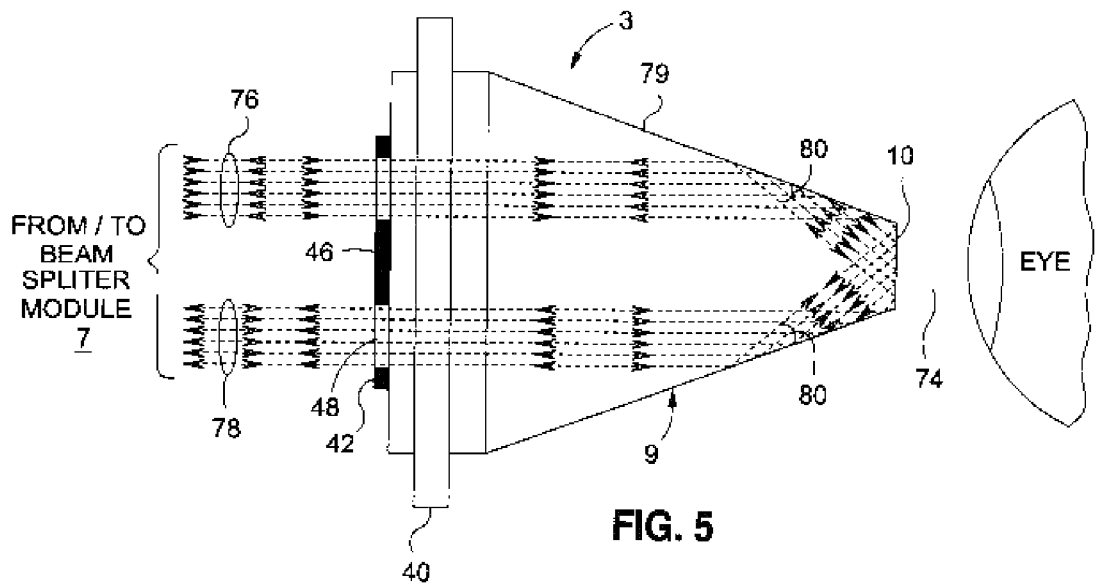
FIG. 5 illustrates the paths of the incoming and reflected light beams with respect to a prism of the applanation tonometer when a contact tip of the prism is spaced from the patient's eye.
Figure 6:
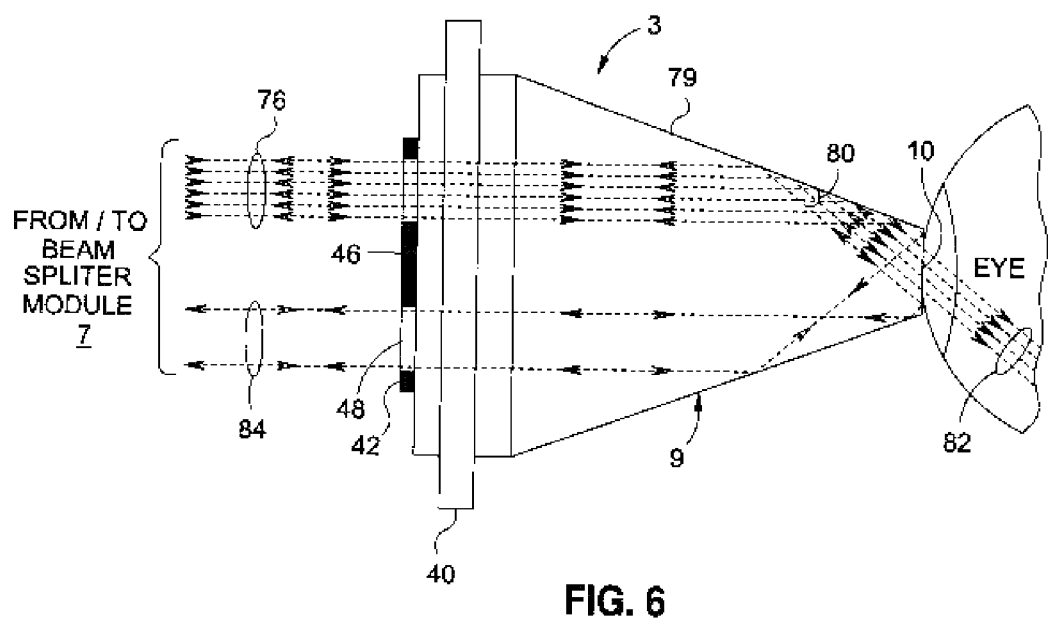
FIG. 6 illustrates the paths of the incoming and reflected light beams with respect to the prism when the contact tip thereof is moved into contact with the cornea of the eye to achieve applanation.

The operation of the applanation tonometer 1 for providing a measurement of the intraocular pressure (IOP) of the patient's eye is explained while now turning to FIGS. 5 and 6 of the drawings. FIG. 5 shows the prism assembly 3 prior to the contact tip 10 of the prism 9 being moved into contact with and applying pressure against the patient's cornea. That is to say, there is initially a space or air gap 74 between the contact tip 10 at the proximal end of prism 9 and the eye. In FIG. 6, the prism assembly 3 is relocated towards the eye so that the contact tip 10 of prism 9 is moved into contact with and presses against the cornea.

With the conical prism 9 separated from the patient's eye by the air gap 74 of FIG. 5, incoming parallel-aligned laser light beams 76 are transmitted from the laser module 5, through the center hole (designated 45 in FIG. 3) of the piezo element 44, around and through the optically-transparent area (designated 48 in FIG. 4) of the light ring 42, and inwardly through the prism 9. In this case, all of the incoming light beams 76 are completely and internally reflected within the prism 9 by the contact tip 10 thereof. Hence, outgoing parallel-aligned laser light beams 78 are reflected off the tapered outer wall 79 and outwardly from the prism 9, around and through the optically-transparent area 48 of the light ring 42, and through the center hole 45 of piezo element 44 for receipt by the photo diode 64 by way of the reflective surface 58 of the beam splitter module 7 of FIG. 3. It is to be understood that the inward and outward light transmission through the optically-transparent area 48 of light ring 42 and the prism 9 occurs circumferentially (i.e., around a full 360 degrees) with respect to the light ring. Therefore, incoming and outgoing light direction arrows illustrated in FIGS. 5 and 6 are shown in both directions.

As explained, both the incoming and reflected light beams 76 and 78 pass around and through the optically-transparent area 48 of the light ring 42 along identical paths. It has been found that the conical prism 9 should be manufactured so that the slope of its tapered outer wall 79 is between 20 to 27 degrees with respect to its longitudinal axis, whereby the incoming parallel-aligned light beams 76 will be reflected off the tapered outer wall 79 and towards (or from) the contact tip 10 so as to make an identical angle 80 of between 20 to 27 degrees with respect to tapered wall 79.

In FIG. 6, the conical prism 9 is moved towards the patient's eye until the air gap (74 of FIG. 5) is eliminated and the contact tip 10 of prism 9 lies in full contact (i.e., applanation) against the cornea regardless of the pushing pressure being in this case, the incoming parallel-aligned laser beams 76 are once again transmitted from the laser module 5, around and through the optically-transparent area 48 of the light ring 42, through the piezo element (44 of FIG. 3), and inwardly through the prism 9 to be reflected at the angle 80 off the tapered outer wall 79 or the prism 9 to the contact tip 10 against the cornea. As the applanation tonometer 1 moves towards saturation (i.e., full contact with the cornea), some of the light beams 82 will be decoupled from the incoming light beams 76 that are reflected at the tapered prism wall 79 to the contact tip 10 of prism 9. The decoupled light beams 82 escape the prism to be absorbed by the patient's eye and are not returned to the photo diode 64.

The outgoing parallel-aligned light beams 84 which are not decoupled from the incoming beams 76 are internally reflected by contact tip 10, first towards the tapered outer prism wall 79, then around and through the optically-transparent area 48 of the light ring 42, through the piezo element 44, and outwardly of the prism 9 for receipt by the photo diode 64 by way of the beam splitter module (7 of FIG. 3).

As will now be explained, the intensity of the outgoing light beams (78 of FIG. 5 and 84 of FIG. 6) internally reflected by the prism 9 to the photo diode 64 prior to, during and after applanation is inversely proportional to the area of touch contact between the contact tip 10 of prism 9 and the opposing surface of the patient's cornea. In other words, the amount or internal reflection by the prism 9 decreases as the contact tip 10 progressively applanates the cornea thus producing a differential signal. When the differential light signal is paired with a differential force signal, information will be available to accurately calculate IOP. In this same regard, it may be appreciated that the decoupled light beams 82 which escape the prism 9 to be absorbed by the eye also depend upon the area of touch contact between contact tip 10 and the cornea.

Figure 7:
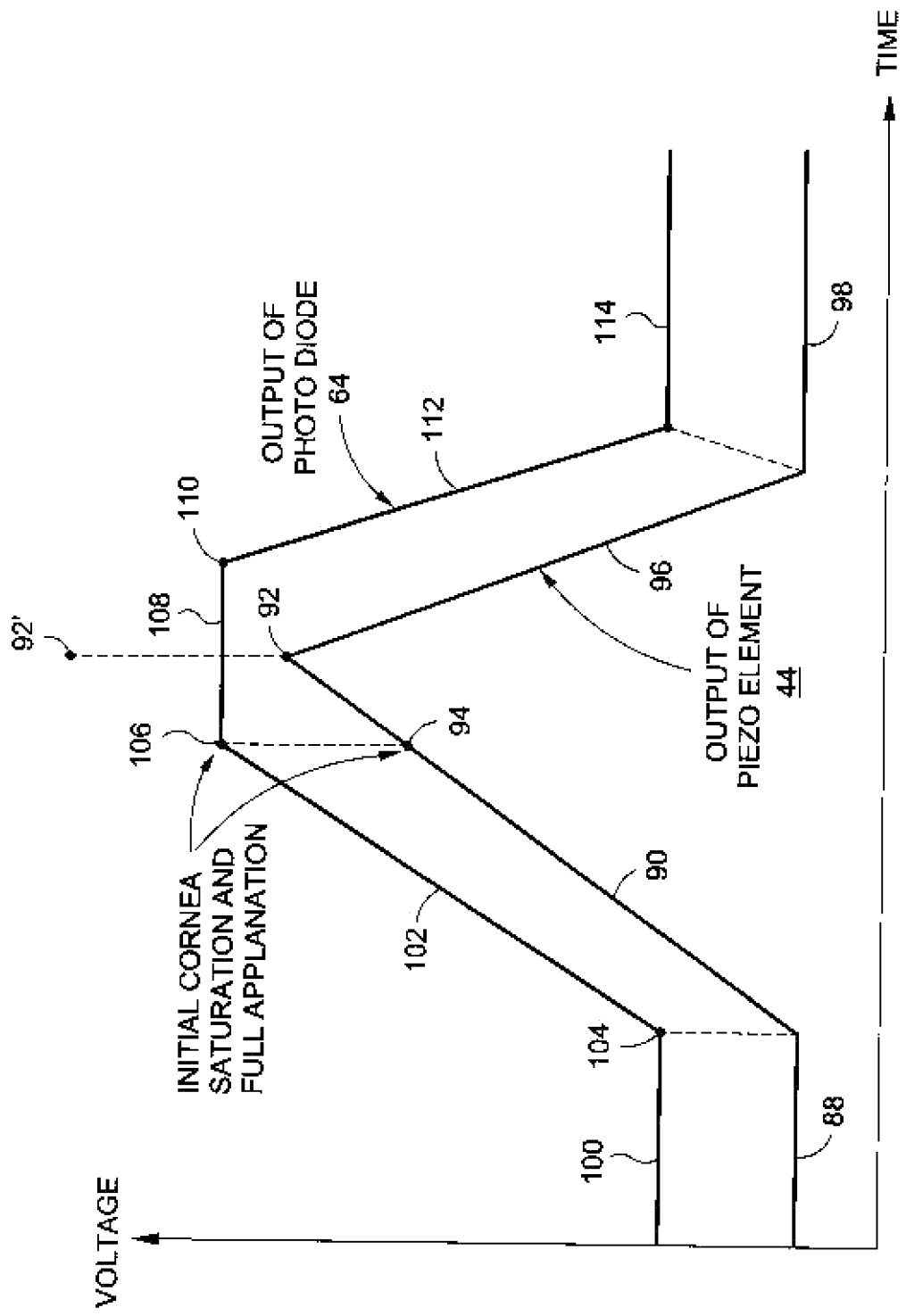
FIG. 7 shows linear representations of the output voltage responses of a piezo element and a photo diode of the applanation tonometer prior to, during and following applanation.

FIG. 7 of the drawings shows graphical (i.e., linear) representations of the voltage responses of the piezo element 44 and the photo diode 64 of the applanation tonometer 1 of FIGS. 1-3 as the prism 9 of prism assembly 3 is moved towards, into contact with, and away from the cornea of the patient's eye. It is to be understood that the responses of the piezo element 44 and the photo diode 64 could also be indicated by resistance rather than voltage. In the present voltage example, the first (bottom most) of the linear representations illustrates the output voltage signal of the piezo element 44 as the pushing force is first increased to achieve full applanation and subsequently diminished following cornea saturation. In particular, a flat baseline voltage 88 is initially set when the prism 9 is spaced from the eye by the air gap 74 shown in FIG. 5 and no pressure is applied to the cornea.

As the contact tip 10 of the prism 9 is pushed harder against the cornea, the contact pressure will increase so that the voltage 90 generated by the piezo electric element 44 correspondingly and continuously increases until a maximum voltage 92 is generated at the apex of touch contact. However, the pushing force (voltage 94) necessary to initially saturate the patient's eye and achieve full applanation is typically less than the maximum pushing force (voltage 92). Following the maximum pushing force (voltage 92) against the cornea, the piezo element 44 will sense a continuously decreasing force and generate a corresponding smaller voltage 96 as the prism 9 is subsequently moved away from the patient's eye and the contact pressure thereagainst is ultimately eliminated so that another flat baseline voltage 98 indicative or no force is generated.

The other (i.e., top most) of the linear representations of FIG. 7 represents the output voltage of the photo diode 64 depending upon the area of touch contact between the contact tip 10 of the prism 9 and the patient's cornea and the corresponding amount of incoming laser light that is transmitted inwardly through prism 9 and decoupled at the contact tip. That is to say, increasing the site of the touch area results in greater decoupling and less light being reflected outwardly through the prism to the photo diode 64.

More particularly, a flat baseline voltage 100 is initially set when the prism 9 is spaced from the eye by the air gap (74 of FIG. 5) such that there is no touch contact between the contact tip 10 and the cornea (when no force is detected by the piezo element 44). As the contact tip 10 of prism 9 is pushed against the cornea, the touch area covered by the contact tip increases. The voltage 102 generated by the photo diode 64 as the reflected light is transmitted outwardly through the prism 9 transitions from a voltage 104 and an area of no touch to a higher voltage 106 and an area of full touch. The initial voltage 106 at the beginning of full touch corresponds with the voltage 94 that is generated by the piezo element 44 under the force at which full applanation first occurs. During the time that the contact tip 10 of the prism 9 is not yet removed from the saturated cornea, a steady voltage 108 (between voltage points 106 and 110) is generated by the photo diode 64 such that the area of the cornea covered by the contact tip 10 remains constant regardless of a pressure increase and the corresponding increase in voltage 92' generated by the piezo element 44. When the prism 9 is removed from the patient's eye, the area covered by the contact tip 10 and the voltage 112 generated by the photo diode 64 will transition lower from the last voltage 110 during full touch contact back to another flat baseline voltage 114 of no touch at which time the pushing force (baseline voltage 98) against the cornea indicated by the piezo element 44 has completely terminated.

Figure 8:
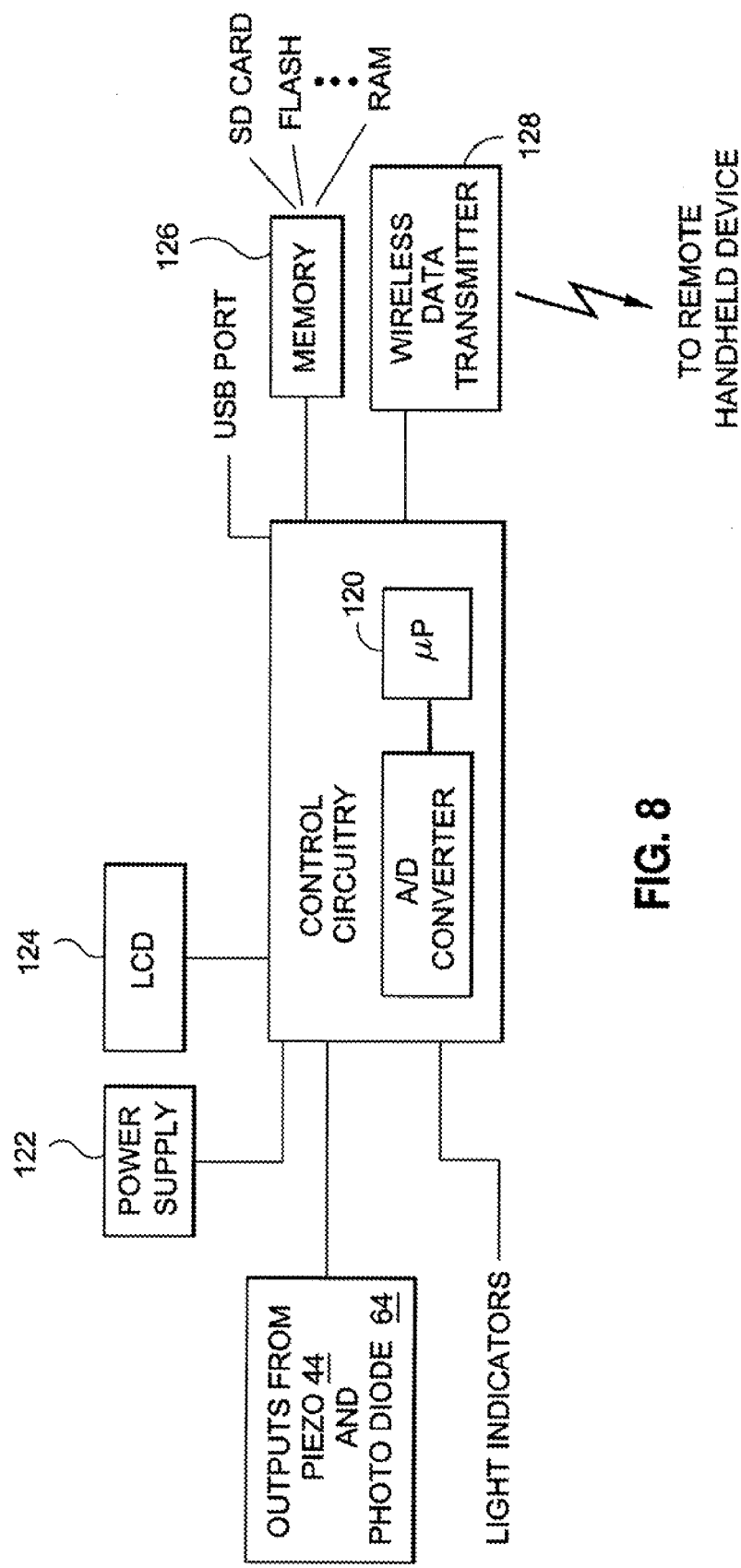
FIG. 8 is a block diagram which is illustrative of means for displaying, storing and processing force/area data derived from the outputs of the piezo element and photo diode of the applanation tonometer.

FIG. 8 of the drawings shows a microprocessor 120 for use at a test site to receive the output signals generated by the piezo element 44 and photo diode 64 of FIG. 3. By way of example only, a suitable microprocessor having an integrated data acquisition system to be used with the applanation tonometer 1 to provide a measurement of IOP is either one of Part Nos. LM12458 or LM12H458 manufactured by National Semiconductor Corporation. Such a microprocessor 120 provides the advantage of combining a fully-differential, self-calibrating 13-bit analog-to-digital converter with a sample-and-hold feature. Programmable data acquisition times and conversion rates are available by means of internal clock-driven timers. The microprocessor is capable of operating from a 5 volt DC (e.g., battery) power supply 122.

The microprocessor 120 can be programmed to display its determination of IOP at an onboard display such as, for example, an LCD display 124. The microprocessor 120 can also control light indicators in order to provide the test administrator with an instantaneous measurement whether the patient's IOP test results represent a passing or failing pressure.

The IOP measurements may be internally computed by the microprocessor 120 at the test site. In this case, the computations may be stored in an onboard memory 126. In the alternative, the computations can be made and/or analyzed (and displayed) by a well-known remote handheld device such as an iPhone, iPad, tablet, and the like. A wireless data transmitter 128 communicates with the remote handheld device over a wireless path.

In general, IOP is determined by a calculation of contact force divided by the area of touch contact represented by the output voltage signal pairs (such as 94 and 106 of FIG. 7) generated by the piezo element 44 and the photo diode 64. The paired force and area measurements can be acquired at greater than 5000 cps. Measurement mean and variance are calculated after only a single touch, although multiple touch data acquisition may be employed. Tissue rigidity may be inferred by analyzing a broad range of force-area pairs between the increasing voltages 90 and 102 of FIG. 7 as applanation is achieved. As with the Goldmann applanation tonometer, a table lookup operation can also be performed on the basis of a nomogram-derived reference of IOP compiled from clinical or laboratory acquired testing measurements taken from a population of human and animal eyes.

However, the applanation tonometer 1 herein disclosed is an improvement over the Goldmann device by allowing for fast and objective area and force measurements with minimal touch contact with the underlying tissue. A short dwell time (typically less than 100 msec) obviates the need in most cases for a topical anesthesia so as to reduce patient safety concerns. With the elimination of moving parts, a jam-free, stable and self-calibrating test environment is available.

The applanation tonometer 1 has been described in its preferred application for measuring IOP inside an eye. However, it is to be understood that use of the tonometer may be extended to include obtaining pressure measurements in botanical tissues, biologically-solid, fluid or air-filled human or animal organs such as blood vessel, stomach, bladder, lung, finger or ankle, and flexible hydrostatic bodies. Moreover, the tonometer can also be used in product and package manufacturing by measuring the pressure of any light-absorbing surface associated there with to predict a fissure or rupture and thereby ensure production quality, shelf-life durability and packaging integrity.

The invention claimed is:

1. An applanation tonometer to measure the intraocular pressure of an eye, said applanation tonometer comprising:
 a light source to generate light;
 a light-transmitting body to receive the light generated by said light source, said light-transmitting body having a contact tip to be moved into contact with the cornea of the eye and apply a pressure thereagainst, such that the light generated from said light source is transmitted in a first direction inwardly through said light-transmitting body to the contact tip thereof so that some of the light transmitted in said first direction is decoupled to escape said light-transmitting body through said contact tip, and the remainder of the inwardly-transmitted light which is not decoupled and does not escape said light-transmitting body is reflected by said contact tip and transmitted in a second direction outwardly through said light-transmitting body;
 a light baffle located between said light source and said light-transmitting body, said light baffle having an optically-opaque inner area, an optically-opaque outer edge spaced from and surrounding said optically-opaque inner area, and a uniformly clear and optically-transparent area extending from said optically-opaque inner area to said optically-opaque outer edge, said light baffle being positioned so that all of the light generated by said light source and transmitted in said first direction inwardly through said light-transmitting body and all of the light reflected by the contact tip of said light-transmitting body and transmitted in said second direction outwardly through said light-transmitting body are transmitted uninterruptedly through the uniformly clear and optically-transparent area of said light baffle;

a photo diode to provide an analog output voltage signal in response to the intensity of the light reflected by said contact tip and transmitted in said second direction through the uniformly clear and optically-transparent area of said light baffle, said photo detector output signal being dependent upon the area of contact between the contact tip of said light-transmitting body and the cornea of the eye;

a force detector to provide an analog output voltage signal in response to the pressure generated at the area of contact after the contact tip of said light-transmitting body is moved into contact with the cornea of the eye and the cornea is fully applanated; and a signal processor including an analog-to-digital converter that is responsive to the analog output voltage signals provided by said photo diode and said force detector to provide a digital indication of the intraocular pressure of the eye depending upon the magnitude of said analog output voltage signals.

2. The applanation tonometer recited in claim 1, wherein said light-transmitting body is a cone.

3. The tonometer recited in claim 1, wherein said light baffle has an optically-opaque inner circle at the optically-opaque inner area thereof, an optically-opaque outer ring at the optically-opaque outer edge, and a uniformly clear and optically-transparent ring at the area extending from said optically-opaque inner circle to said optically-opaque outer ring, such that all of the light transmitted in said first and second directions through said light-transmitting body passes uninterruptedly and only through the uniformly clear and optically-transparent ring of said light baffle.

4. The tonometer recited in claim 3, wherein the size of the optically-opaque inner circle of said light baffle is identical to the size of the contact tip of said light-transmitting body.

5. The applanation tonometer recited in claim 2, wherein said light-transmitting cone has an outer wall which slopes from a wide first end of said cone adjacent which said force detector is located to a narrow opposite end at which said contact tip is located so that the light generated by said light source and transmitted in said first direction inwardly through said cone is reflected off said sloping outer wall to said contact tip at an ale of between 20 to 27 degrees with respect to said sloping outer wall.

6. The applanation tonometer recited in claim 2, wherein said force detector is a piezo element aligned with said light-transmitting cone and having an opening formed therein so that the light generated by said light source passes through said opening to said cone.

7. The applanation tonometer recited in claim 2, further comprising a beam splitter located between said light source and said light-transmitting cone so that the light generated by said light source is transmitted to said cone by way of said beam splitter, said beam splitter having a reflective surface aligned to reflect to said photo diode the light which is reflected by the contact tip of said cone in said second dire ion outwardly through said cone.

8. A tonometer to measure the pressure at a light-absorbing surface of a flexible hydrostatic body, said tonometer comprising:

a light source to generate light;

a light-transmitting cone positioned to receive the light generated by said light source such that said light is transmitted in a first direction inwardly through said cone, said cone having a contact tip to be moved into contact with the light-absorbing surface of the hydrostatic body and apply a pressure thereagainst, and said contact tip positioned to receive the light transmitted inwardly through said cone in said first direction and to reflect at least some of said inwardly-transmitted light in a second direction outwardly through said cone depending upon the area of contact between the contact tip of said cone and said light-absorbing surface;

a light baffle located between said light source and said cone, said light baffle having an optically-opaque inner area, an optically-opaque outer edge spaced from and surrounding said optically-opaque area inner area, and a uniformly clear and optically-transparent area, extending from said optically-opaque inner area to said optically-opaque outer edge, said light baffle being positioned so that all of the light generated by said light source and transmitted in said first direction inwardly through said cone and all of the light reflected by the contact tip of said cone and transmitted in said second direction outwardly through said cone are uninterruptedly transmitted through the optically-transparent area of said light baffle;

a photo detector to receive the light reflected by said contact tip in the second direction outwardly through said cone and through the uniformly clear and optically-transparent area of said light baffle so as to provide an analog output voltage signal in response to the intensity of the light received by said photo detector in said second direction;

a force detector to provide an analog output voltage signal in response to the pressure generated at the area of contact by the contact tip of said cone moving into contact with the hot-absorbing surface; and a signal processor including an analog-to-digital converter that is responsive to the analog output voltage signals provided by said photo detector and said force detector to provide a digital indication of the pressure of the light-absorbing surface depending upon the magnitude of said analog output voltage signals.

9. The tonometer recited in claim 8, wherein the size of the contact tip of said light-transmitting cone and the size of the optically-opaque inner area of said light baffle are identical.

10. The tonometer recited in claim 8, wherein said light-transmitting cone has an outer wall which slopes from a wide first end adjacent which said force detector is located to a narrow opposite end at which said contact tip is located so that the light generated by said light source and transmitted in said first direction inwardly through said cone is reflected off the sloping outer wall thereof towards said contact tip at said narrow end of said cone at an angle with respect to said sloping outer wall between 20 to 27 degrees.

11. The tonometer recited in claim 8, further comprising a beam splitter having a reflective surface, wherein said beam splitter has an opening formed therein, said photo detector located in said opening such that the reflective surface of said beam splitter is aligned to reflect the light being reflected in the second direction by the contact tip of said light-transmitting cone to said photo detector.

12. The tonometer recited in claim 8, wherein all of the light transmitted in the first direction inwardly through said light-transmitting cone and all of the light transmitted in the second direction outwardly through said light-transmitting cone travel along identical optical paths through the uniformly clear and optically-transparent area of said light baffle.

13. A method for measuring the intraocular pressure of an eye, said method comprising the steps of:
- transmitting light from a light source in a first direction inwardly through a prism having a contact tip;
- locating a light baffle between said light source and said prism, said light baffle having an optically-opaque inner area, an optically-opaque outer edge spaced from and surrounding said optically-opaque inner area, and a uniformly clear and optically-transparent area extending from said optically-opaque inner area to said optically-opaque outer edge, wherein the size of the optically-opaque inner area of said light baffle is identical to the size of the contact tip of said prism;
- moving the contact tip of said prism into contact with the cornea of the eye so as to apply a pressure against the eye, such that all of the light being transmitted from said light source in said first direction inwardly through said prism is supplied uninterruptedly through the uniformly clear and optically-transparent area of said light baffle to said contact tip at which some of said inwardly transmitted light is decoupled to escape said prism through said contact tip, and all of the remainder of said light which is not decoupled and does not escape the prism is reflected by said contact tip and transmitted in a second direction outwardly through said prism by first passing uninterruptedly through the uniformly clear and optically-transparent area of said light baffle;
- providing a first signal in response to the intensity of the light reflected by said contact tip and transmitted in said second direction outwardly through said prism by way of the uniformly clear and optically-transparent area of said light baffle, said output signal being dependent upon the area of contact of the contact tip of said prism with the cornea of the eye;
- providing a second signal in response to the pressure generated at the area of contact by the contact tip of the prism lying in contact with the cornea of the eye so that the cornea is fully applanated; and
- transmitting said first and second signals to a signal processor and processing said signals for providing the measurement of the intraocular pressure of the eye depending upon said first and second signals.

* * * * *